United States Patent [19]

Collins et al.

[11] Patent Number: 4,801,450
[45] Date of Patent: * Jan. 31, 1989

[54] HIGH TITER PSEUDOMONAS IMMUNE SERUM GLOBULIN

[75] Inventors: Michael S. Collins; Robert E. Roby, both of Pinole, Calif.

[73] Assignee: Miles Laboratories, Inc., Elkhart, Ind.

[*] Notice: The portion of the term of this patent subsequent to May 6, 2003 has been disclaimed.

[21] Appl. No.: 859,944

[22] Filed: May 5, 1986

Related U.S. Application Data

[63] Continuation-in-part of Ser. No. 504,106, Jun. 14, 1983, Pat. No. 4,587,121.

[51] Int. Cl.$^4$ ............................................. A61K 39/40
[52] U.S. Cl. ...................................... 424/87; 424/85.8; 514/387
[58] Field of Search .................... 424/85, 87; 514/387

[56] References Cited

U.S. PATENT DOCUMENTS

| | | | |
|---|---|---|---|
| 2,793,203 | 5/1951 | Schultze et al. | 424/85 |
| 4,027,010 | 4/1975 | Kiseler et al. | 424/87 |
| 4,120,950 | 10/1978 | Homna | 424/87 |
| 4,285,936 | 8/1981 | Peer et al. | 424/88 |
| 4,482,483 | 11/1984 | Curry et al. | 424/87 |

*Primary Examiner*—Blondel Hazel
*Attorney, Agent, or Firm*—James A. Giblin

[57] ABSTRACT

Normal plasma from donors who have not been vaccinated with a Pseudomonas vaccine or had a Pseudomonas infection can be screened for higher than normal titers of naturally occurring antibody to four or, preferably, two of seven Fisher Immunotypes of Pseudomonas. Those plasmas with higher titers of such antibody can be pooled and fractionated to give hyperimmune serum globulin having high titers of antibody against all seven Fisher Immunotypes. The product may be treated to render it intravenously injectable and the so-prepared material is effective in treating patients with Pseudomonas infection. Also disclosed is a novel antibody preparation including minimum titers of the seven Fisher Immunotypes.

17 Claims, No Drawings ent of Ser. No. 504,106 filed on June 14, 1983, now U.S. Pat. No. 4,587,121.

HIGH TITER PSEUDOMONAS IMMUNE SERUM GLOBULIN

This is a continuation-in-part of Ser. No. 504,106 filed on June 14, 1983, now U.S. Pat. No. 4,587,121.

BACKGROUND OF THE INVENTION

1. Field of the Invention

This invention relates to and has among its objects novel immune serum globulins and novel methods for their production. Particularly, the invention is concerned with immune serum globulins having a high titer of naturally occurring antibody to lipopolysaccharide antigens of *Pseudomonas aeruginosa*. Further objects of the invention will be evident from the following description wherein parts and percentages are by weight unless otherwise specified.

2. Description of the Prior Art

Hyperimmune serum globulins, i.e., immune serum globulin having high titers of a particular antibody, are therapeutically useful in treating patients with antibody immunodeficiency. For example, tetanus hyperimmune globulin is useful in treating tetanus and rabies hyperimmune globulin, rabies. It is well known that hyperimmune serum globulins can be produced from plasma or serum obtained from selected donors who have much higher titers for a specific antibody than is normally found in the average population. These donors have either been recently immunized with a particular vaccine (U.S. Pat. No. 4,174,388) or else they have recently recovered from an infection or disease [Stiehm, *Pediatrics*, Vol. 63, No. 1, 301–319 (1979)]. These high titer sera or plasmas are pooled and subjected to the usual Cohn fractionation procedures up to the point of isolating Fraction II [Cohn et al, *J. Am. Chem. Soc.*, 68, 459 (1946) and Oncley, et al, ibid., 71, 541 (1949)].

Although infection with *Pseudomonas aeruginosa* (*P. aeruginosa*) is not common among the general population, *P. aeruginosa* infection is encountered very frequently in certain susceptible groups of patients. Burn victims and immunosuppressed cancer patients have been identified as having an unusually high risk of acquiring severe, and sometimes fatal, *P. aeruginosa* infection. *P. aeruginosa* infections are usually acquired during a hospital stay, not at home.

P. aeruginosa is resistant to penicillin G. A combination of *P. aeruginosa* specific penicillin and an aminoglycoside is the usual therapy for *P. aeruginosa* sepsis and has greatly contributed to the survival of patients, particularly leukemics. The management of *P. aeruginosa* in burn patients is also dependent upon topical antimicrobial therapy.

James et al, in *The Lancet*, 13 December 1980, 1263–1265, described passive immunization of burn patients at risk of septicaemia. The immunization was accomplished with an immunoglobulin prepared from plasma from healthy human volunteers vaccinated with a polyvalent Pseudomonas vaccine. There is, of course, some risk in vaccinating healthy volunteers in order to increase their titer of antibody in plasma.

Zaia et al in *The Journal of Infectious Diseases*, Vol. 137, No. 5, 601–604 (1978) disclosed a practical method for preparation of Varicella-Zoster (VZ) Immune Globulin. Outdated blood was screened for complement-fixing antibody to VZ virus. About 15% of the plasma units had a titer greater than or equal to 16, with about 7.5% greater than or equal to 32.

Fisher et al have identified seven non-cross-protective immunotypes of *P. aeruginosa* (Fisher et al, *Journal of Bacteriology*, May 1969, p. 835–836, which is incorporated herein by reference). The authors developed an antigen scheme for *P. aeruginosa* based on challenge protection in mice as distinguished from serological tests *in vitro*.

SUMMARY OF THE INVENTION

We have found that normal plasma from donors who have not been vaccinated with a Pseudomonas vaccine or had a recent Pseudomonas infection can be screened for higher than normal titers of antibody to four or, preferably, two of the seven immunotypes (Fisher et al) in *P. aeruginosa*. Those plasmas with titers greater than about 1:1600 can be pooled and then fractionated to give a *P. aeruginosa* hyperimmune gamma globulin that has a high titer of antibody to lipopolysaccharide antigens of all seven Fisher immunotypes and can offer significant protection against all seven of the Fisher immunotypes. This result is quite surprising because it is unexpected that plasma from normal donors not vaccinated or not having had a recent Pseudomonas infection would have a titer of antibody to *P. aeruginosa* high enough to yield, when pooled and fractionated, a Pseudomonas hyperimmune globulin which shows significant effectiveness in treating *P. aeruginosa* infections. Furthermore, it is surprising that screening for only four or, preferably, two of the seven Fisher immunotypes and pooling the plasma reflecting higher than normal titers for only four of the seven Fisher immunotypes would yield a hyperimmune serum globulin that provides significant protection against all seven of the Fisher immunotypes. We have also found that we can prepare a novel antibody (gamma globulin) preparation having a titer of unattenuated (native or un-modified) antibody to Fisher immunotypes 1, 2, 3, 4, 6 and 7 of at least 1:6400 and to Fisher immunotype 5 of at least 1:3000.

One obvious advantage of the invention is that normal donors need not be given a vaccine. Consequently, any risks inherent in such a practice are avoided. Another advantage of the invention is that the hyperimmune globulin obtained offers immediate protection and may be treated to render it intravenously injectable, thus avoiding patient discomfort associated with intramuscular administration. Furthermore, less product need be administered intravenously in order to achieve the same level of prevention or cure obtained with an intramuscularly administered product.

DESCRIPTION OF THE PREFERRED EMBODIMENTS

These and other advantages of the present invention may be obtained in the following manner.

Normal plasma from a donor is screened for naturally occurring antibody to lipopolysaccharide antigens of *P. aeruginosa* of Fisher immunotypes 1, 2, 4, and 6 or, preferably, only immunotypes 1 and 6, employing an enzyme-linked immunosorbent assay (ELISA) or other equally sensitive screening method such as radioimmune assay, etc. To be significantly effective it has been found that the plasma from such donors should have a titer of antibody to the aforementioned Fisher immunotype combinations greater than about 1:1600. About 2–5% of plasma donors have such titers. A hyperimmune serum globulin obtained in this manner contains higher than normal titers of antibody to all seven Fisher immunotypes and can be significantly effective against all seven of the Fisher immunotypes for *P. aeruginosa*, thus, being effective in treating patients suffering from *P. aeruginosa* infection.

The method of screening the plasma, i.e., the ELISA method, is essentially as described by Engvall and Perlmann, *J. Immunol.*, 109, 129–135 (1972), Engvall et al, *Biochemica Et Biophysica Acta*, 251 (1971) 427–434, Engvall et al, *Immunochemistry*, 8, 871–874 (1971), Voller et al, *Bull. World Health Organ.*, 51, 209–211, (1974), and Voller et al, *ibid.*, 53, 55–65 (1976) which are all incorporated herein by reference. The assay is a simple method for the quantitative determination of antibodies. Wells of polystyrene 96 well microtiter plates coated with antigen are incubated with antiserum followed by an enzyme-labeled preparation of anti-immunoglobulin. The enzyme remaining in the tubes after washing provides a measure of the amount of specific antibodies in serum. Using the ELISA method 1–100 nanograms/ml of antibody can be determined.

Plasma having a sufficiently high titer of antibody to Fisher immunotypes 1, 2, 4, and 6 or, preferably only immunotypes 1 and 6, of *P. aeruginosa* is pooled and fractionated to obtain an immune serum globulin. To this end one may employ any method for obtaining an intravenously injectable immune serum globulin from pooled plasma. For example, one may employ the Cohn fractionation method (referenced hereinabove, which references are incorporated herein by reference thereto) to give Cohn Fraction II, ammonium sulphate fractionation, gel chromatography, semipermeable membrane filtration, or the like. The immune serum globulin of the invention has a titer of antibody to Fisher immunotypes 1, 2, 4, and 6 (or immunotypes 1 and 6) of at least 1:6400 and to Fisher immunotypes 3, 5, and 7 of at least 1:1600. The aforementioned immune serum globulin comprises IgG, usually at least 90% of IgG monomer. The material generally also contain other gamma globulins such as IgA, IgM, and the like.

As mentioned above, the *P. aeruginosa* hyperimmune globulin may be intramuscularly or intravenously injectable. The latter material is preferred and may be prepared, for example, according to the method of U.S. Pat. No. 3,903,262 (which is incorporated herein by reference) or any of the methods referred to in the above-identified U.S. patent. The modified immune serum globulin of U.S. Pat. No. 3,903,262 is adapted for intravenous injection and consists of intact immune serum globulin chains having partly intact interchain disulfide linkages. Each cleaved disulfide linkage is replaced by a pair of alkylated mercapto groups, the cleaved chains remaining united by non-covalent association so that the apparent molecular weight of the modified serum globulin in non-dissociating solvents is substantially the same as unmodified immune serum globulin. The above material is produced by selectively reducing a mildly alkaline aqueous solution of an immune serum globulin with dithiothreitol or dithiolrythritol, alkylating the thus-reduced interchain disulfide groups, and separating the thus-modified globulin from the non-proteinaceous reaction products. It is also appreciated that the *P. aeruginosa* may be prepared for intravenous infusion by low pH methodology (pH of 3.5 to 5.0) according to U.S. Pat. No. 4,396,608 issued Aug. 2, 1983 in the name of R. Tenold.

The hyperimmune globulin preparation of this invention can also include maltose as a stabilizer in accordance with the teaching of U.S. Pat. No. 4,186,192. Accordingly, the instant preparation may contain about 1–20% of maltose on a weight to volume basis.

The hyperimmune products of the invention may be incorporated into pharmaceutical preparations, usually aqueous solutions of the hyperimmune serum globulin which may be used for therapeutic purposes. However, the term "pharmaceutical preparation" is intended in a broader sense herein to include preparations containing a hyperimmune serum globulin in accordance with this invention used not only for therapeutic purposes, but also for reagent purposes as known in the art; for tissue culture wherein organisms such as viruses for the production of vaccines and the like, are grown on plasma or on plasma fractions, e.g., Cohn Effluent II + III, Cohn Fraction IV, Cohn Fraction V, and so forth; etc.

The pharmaceutical preparation intended for therapeutic use should contain a therapeutic amount of hyperimmune serum globulin, i.e., that amount necessary for preventative or curative health measures. If the pharmaceutical preparation is to be employed as a reagent, then it should contain reagent amounts of hyperimmune serum globulin. Similarly, when used in tissue culture or a culture medium the preparation should contain an amount of hyperimmune serum globulin sufficient to obtain the desired growth.

EXAMPLES

Screening for Fisher Immunotypes 1, 2, 4 and 6

The invention is demonstrated further by the following illustrative examples.

Assay Method

The assay method was essentially the same as that described by Voller et al, supra. Two hundred microliters (200 $\mu$l) of antigen (5 $\mu$g/ml) in carbonate buffer pH 9.6 was added to each well of polystyrene microtiter plates and incubated at 37° C. for 3 hours. The plates were washed once with phosphate buffered saline (PBS) containing 0.05% Tween 20 and allowed to drain. Serum was diluted in PBS-Tween. Fifty (50) $\mu$l of PBS-Tween 20 was added to each well. An initial dilution of serum (1:50) was made in a Wasserman tube. Serial two-fold dilutions were made from this dilution in a microtiter plate using a 50 $\mu$l microtiter loop. The first dilution in the plate was 1:100. After completion of the serial two-fold dilutions, the volume in the wells was made up to 200 $\mu$l with 150 $\mu$l of PBS Tween 20. The final dilution in each well was thus increased four-fold. The plates were incubated overnight at room temperature and then washed three times. Two hundred (200) $\mu$l of goat anti-human IgG conjugated to alkaline phosphotase diluted 1:1000 in PBS- Tween 20 was added to the wells and incubated at room temperature for 4 hours. After washing the plates four times with PBS Tween 20, 200 $\mu$l of enzyme substrate p-nitrophenylphosphate (Sigma Chemical Co., Saint Louis, Mo.) 1 mg/ml of diethanolamine buffer was added to each well and was allowed to incubate at room temperature for 30 minutes. The yellow color which developed was quantitated spectrophotometrically at 405 nm. A dilution of normal serum at 1:1,600 gave absorbence (OD) readings less than 0.05. Therefore, a serum diluted 1,600 having an OD reading of 0.1 or greater is considered positive.

The materials and reagents employed in the above procedure were:
PBS-Tween 20 —with 0.05% Tween 20.

Carbonate buffer—0.06 M; pH 9.5–1.91 g Na$_2$CO$_3$, 3.52 g NaHCO$_3$ in 1 liter of distilled water.

Diethanolamine buffer 10%; pH 9.8—pH adjusted with 1 M HCL. (Note: 0.02% NaN$_3$ was added to the above reagents to prevent bacterial growth).

Goat anti-human IgG conjugated with alkaline phosphotase (Miles Laboratories, Elkhart, Ind.).

Polystyrene microtiter plates—Dynatech Laboratories Cat. #1-220-24X.

12—channel pipette and multi-tips, Flow Laboratories Cat. #77-889-00.

EXAMPLE 1

Plasma obtained from donors was screened for titer to antibody to Fisher immunotypes 1, 2, 4, and 6 *P. aeruginosa* using the above-described ELISA method. Titer is that dilution giving an OD$_{405nm}$ ≧ 0.1.

Plasma with a *P. aeruginosa* Fisher immunotypes 1, 2, 4, and 6 titer of 1:1600 or greater were pooled. The pooled sera (0.1 ml) were used to passively immunize mice three hours before challenge with 20 LD$_{50}$ of *P. aeruginosa*. (20 LD$_{50}$=20× the dose needed to kill 50% of challenged mice).

As controls, pools of sera were prepared having a titer of antibody to *P. aeruginosa* of less than 1:400, 1:400, and 1:800. Mice were similarly injected with one of these pooled sera prior to challenge with 20 LD$_{50}$ of *P. aeruginosa* as mentioned above.

The results are summarized in Table 1.

TABLE 1

| ELISA titer | Sera in Pool No. | % Total | Cumulative Mortality | P[a] |
|---|---|---|---|---|
| <1:400 (control) | 160 | 64.5 | 10/10 | |
| 1:400 (control) | 41 | 16.5 | 8/10 | NS[b] |
| 1:800 (control) | 24 | 9.7 | 8/10 | NS |
| 1:1600 | 23 | 9.3 | 4/10 | .05 |

[a]Statistical significance.
[b]NS is not significant protection by chi-square test.

EXAMPLE 2

Sixteen donors from Example 1 donated additional plasma 1–3 months after the donation of Example 1. The titer of antibody to *P. aeruginosa* by ELISA in eight sera samples was 1:1600 or greater; in the other eight samples the titer was 1:800 or greater.

The pooled sera were injected into mice as in Example 1 and the mice challenged with *P. aeruginosa* as above. Sera with a titer less than 1:400 and saline were the controls.

The results are summarized in Table 2.

TABLE 2

| ELISA titer | Sera in Pool No. | Cumulative Mortality | % Mortality | P |
|---|---|---|---|---|
| 1:400 (control) | 160 | 46/60 | 76.7 | NS |
| 1:800 | 8 | 88/160 | 55.0 | .004 |
| 1:1600 | 8 | 53/155 | 34.2 | .0001 |
| Saline (control) | — | 30/38 | 78.9 | |

EXAMPLE 3

The pooled sera with titer of antibody to Fisher immunotypes 1, 2, 4, and to *P. aeruginosa* of 1:1600 or greater was fractionated to give an intravenous immune serum globulin (IGIV). The ammonium sulfate fractionation method of Heide et al, "Handbook of Experimental Immunology", 3rd edition, 1979I, was employed. 880 mg total protein was purified by chromatography on Sephadex G-200 530 ml column. As a control, normal sera was fractionated by the above method to produce an IGIV.

The antibody distributions of the hyperimmune IGIV of the invention and the control are summarized below in Table 3.

TABLE 3

| | Antibody titer$^{-1}$ by ELISA | | |
|---|---|---|---|
| Fisher Immunotype | Hyperimmune Pseudomonas[a] IGIV 5% | Normal IGIV 5% | Antibody Increase (× fold) |
| 1 | 6,400 | 800 | 8 |
| 2 | 6,400 | 1,600 | 4 |
| 3 | 3,200 | 800 | 4 |
| 4 | 12,800 | 800 | 16 |
| 5 | 3,200 | 800 | 4 |
| 6 | 6,400 | 800 | 8 |
| 7 | 6,400 | 1,600 | 4 |

[a]Prepared from equal volumes of plasma screened for IgG to immunotypes 1, 2, 4, and 6.

EXAMPLE 4

The so-fractionated hyperimmune Pseudomonas IGIV of Example 3 as well as sera from Example 3 were administered to mice as described in Example 1 and the mice challenged as in Example 1.

The results are summarized in Table 4.

TABLE 4

| ELISA titer | Cumulative mortality after 3 days |
|---|---|
| IgG (1:6400) | 2/10 |
| Sera (1:1600) | 4/10 |
| Sera (1:400) | 9/10 |

Screening for Immunotypes 1 and 6

In the above disclosure hyperimmune human plasma for the production of Pseudomonas-IGIV is acquired by screening plasma of normal donors against monovalent lipopolysaccharide (LPS) of *P. aeruginosa* in an ELISA. The above procedure entails screening human plasma against Fisher immunotypes 1, 2, 4 or 6 individually resulting in four distinct plasma pools. Equal volumes of the four pools are blended and fractionated. Although this method has proven to be practical, it is complex logistically, and it tends to be inefficient, time consuming and costly.

Rather than screen plasma against a single antigen, we have also recently found a better and more efficient way is to screen plasma against a bivalent antigen consisting of 5 μg each of immunotypes 1 and 6 LPS. This method hinges on the demonstration that donors having high levels of antibody to immunotype 1 or 6 generally have high levels of antibody to immunotypes 2 or 4. Moreover, antibody levels against immunotypes 1 and 6 are found less frequently than antibody to immunotypes 2 and 4 in the donor population and generally at lower levels. The bivalent 1 and 6 antigen ELISA balances this situation by giving preference to these two immunotypes in the selection process.

EXAMPLE 5

To date 165 plasma samples have been selected against the bivalent 1 and 6 LPS antigen, pooled and tested by ELISA for potency against 7 Fisher immunotypes compared with potency of the reference plasma of P5150 PS-IGIV, the first lot of immunoglobulin that was prepared using the monovalent antigen method. The results are shown below:

TABLE 5

| Fisher Immunotype | P5150 Plasma Pool (standard)* | Bivalent Plasma Pool | Bivalent Potency Antibody units/ml |
|---|---|---|---|
| 1 | 2,264 | 4,696 | 1.93 |
| 2 | 4,474 | 9,115 | 2.04 |
| 3 | 978 | 2,544 | 2.61 |
| 4 | 3,505 | 3,811 | 1.09 |
| 5 | 591 | 819 | 1.38 |
| 6 | 2,143 | 3,301 | 1.45 |
| 7 | 1,859 | 3,216 | 1.79 |

*The standard contains 1 unit of antibody per ml.

This improved method reduces the time required for screening donors by 75%. It improves potency and reduces the cost of plasma screening. The donor acceptance rate for this new method is approximately 5.4% of all screened donors. Thus, this approach is now our preferred method for obtaining a high titer ISG product.

EXAMPLE 6

Normal plasma from a donor is screened for naturally occurring antibody to Fisher immunotypes 1 and/or 6. The screening lipopolysaccharide antigen consists of carbonate buffer containing 5 μg/ml immunotype to lipopolysaccharide. The antigen is thus bivalent. A serum is positive if a 1:1600 dilution gives an OD reading greater 0.100 at 405 nm. In all other respects, the ELISA is identical to the examples described above.

TABLE 6

| | Antibody Titer by ELISA | | |
|---|---|---|---|
| Fisher Immunotype | Normal IGIV 5% | Hyperimmune[a] Pseudomonas IGIV 5% | Bivalent[b] Pseudomonas IGIV 5% |
| 1 | 800 | 6,400 (8)[c] | 12,800 (16) |
| 2 | 1,600 | 6,400 (4) | 32,000 (20) |
| 3 | >400, >800 | 800 (~2) | 12,000 (~15) |
| 4 | 800 | 12,800 (16) | 16,000 (20) |
| 5 | >400, >800 | 800 (~2) | 5,000 (~6) |
| 6 | 800 | 6,400 (4) | 16,000 (20) |
| 7 | 800 | 1,600 (2) | 10,000 (12) |

[a]Prepared from equal volumes of plasma screened for IgG to immunotypes 1, 2, 4 and 6.
[b]Prepared from one pool of plasma screened for IgG to bivalent immunotypes 1, 6 antigen.
[c]Antibody increase (x fold) over normal IGIV.

A preferred antibody preparation has titers to each of Fisher immunotypes 1, 2, 3, 4, 6 and 7 of at least about 1:6,400 and to Fisher immunotype 5 of at least 1:5,000. This antibody preparation is preferably adapted for intravenous administration by known means such as the reduction/alkylation method or, more preferably, the low pH method of U.S. Pat. No. 4,396,608 in which case the antibody preparation has a pH in the range of about 3.5 to 5.0.

What is claimed is:

1. A method for preparing an immune serum globulin having a high titer of antibody to lipopolysaccharide antigens of P. aeruginosa of Fisher immunotypes 1-7 which comprises
   (a) screening plasma from donors who have not been vaccinated with a Pseudomonas vaccine or had a recent Pseudomonas infection for a titer of unattenuated antibody to lipopolysaccharide of P. aeruginosa of Fisher immunotypes 1 and 6 which is about 1:1,600 or greater,
   (b) pooling plasma of said titer of antibody, and
   (c) preparing an immune serum globulin from said pooled plasma.

2. The method of claim 1 which further includes the step of rendering the immune serum globulin of step c intravenously injectable.

3. The method of claim 1 wherein donor plasma is screened by an enzyme-linked immunosorbent assay.

4. The method of claim 1 wherein the immune serum globulin is produced by the Cohn fractionation method.

5. The method of claim 1 wherein the immune serum globulin is produced by an ammonium sulfate fractionation method.

6. The method of claim 1 wherein the immune serum globulin is reduced and alkylated to render it intravenously injectable.

7. The method of claim 1 wherein the immune serum globulin comprises IgG.

8. An immune serum globulin having a titer of antibody to lipopolysaccharide antigens of P. aeruginosa of Fisher immunotypes 1 and 6 of at least 1:1,600 produced by the method of claim 1.

9. The immune serum globulin of claim 8 having a titer of antibody to lipopolysaccharide antigens of P. aeruginosa of Fisher immunotypes 1-7 sufficient to render the immune serum globulin effective in treating P. aeruginosa infections.

10. A pharmaceutical preparation for treating patients with pseudomonas infection comprising an aqueous solution of the immune serum globulin of claim 8.

11. The preparation of claim 10 which further includes maltose.

12. The immune serum globulin of claim 8 which is intravenously injectable and is in aqueous solution having a pH ranging from about 3.5 to about 5.0.

13. An antibody preparation having titers of antibodies to each of Fisher immunotypes 1, 2, 3, 4, 6 and 7 of at least 1:6,400 and to Fisher immunotype 5 of at least about 1:5,000.

14. The preparation of claim 13 wherein the preparation is adapted for intravenous administration.

15. The preparation of claim 14 wherein the preparation is stabilized with a carbohydrate.

16. The preparation of claim 14 wherein the carbohydrate is maltose.

17. The preparation of claim 13 wherein the preparation is in aqueous solution and has a pH ranging from about 3.5 to about 5.0.

* * * * *